United States Patent [19]

Smith

[11] 4,147,877

[45] Apr. 3, 1979

[54] ω-ARYL-6-HYDROXY-PGE$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 918,522

[22] Filed: Jun. 23, 1978

Related U.S. Application Data

[63] Continuation-in-part of Ser. No. 812,794, Jul. 5, 1977, Pat. No. 4,131,738.

[51] Int. Cl.$^2$ .............................................. C07C 177/00
[52] U.S. Cl. ...................................... 560/53; 562/464
[58] Field of Search .......................... 560/53; 562/464

*Primary Examiner*—Paul J. Killos
*Attorney, Agent, or Firm*—Robert A. Armitage

[57] ABSTRACT

The present invention provides ω-aryl-6-hydroxy-PGE$_1$ compounds which are useful pharmacological agents. These analogs are useful as prostacyclin-like drugs.

83 Claims, No Drawings

ω-ARYL-6-HYDROXY-PGE₁ COMPOUNDS

CROSS REFERENCE TO RELATED APPLICATION

This application is a continuation-in-part of Ser. No. 812,794, filed July 5, 1977, now issued a U.S. Pat. No. 4,131,738.

The present invention relates to ω-aryl-6-hydroxy-PGE₁ compounds, the preparation and use of which are described in U.S. Ser. No. 812,794, filed July 5, 1977, now issued as a U.S. Pat. No. 4,131,738 on Dec. 26, 1978.

The essential material constituting a disclosure of the instant invention is incorporated by reference here from U.S. Pat. No. 4,131,738.

I claim:

1. A prostacyclin analog of the formula

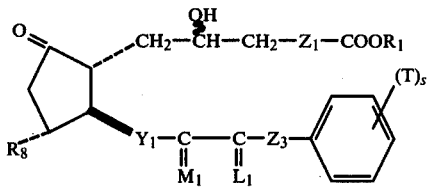

wherein $Z_1$ is
(1) $-(CH_2)_g-CH_2-CH_2-$,
(2) $-(CH_2)_g-CH_2-CF_2-$, or
(3) trans-$(CH_2)_g-CH=CH-$,
wherein g is the integer one, 2, or 3;
wherein $Y_1$ is
(1) trans-CH=CH—,
(2) cis-CH=CH—,
(3) —CH₂CH₂—,
(4) trans-CH=C(Hal)—, or
(5) —C≡C—,
wherein Hal is chloro or bromo;
wherein $M_1$ is

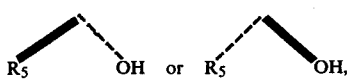

wherein $R_5$ is hydrogen or alkyl with one to 4 carbon atoms, inclusive;
wherein $L_1$ is

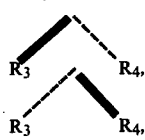

or a mixture of

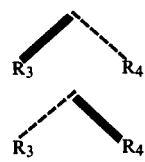

and wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

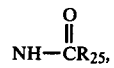
(a)

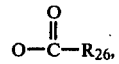
(b)

(c)

(d)

wherein $R_{25}$ is methyl, phenyl, acetamidophenyl, benzamidophenyl, or —NH₂; $R_{26}$ is methyl, phenyl, —NH₂, or methoxy; and $R_{27}$ is hydrogen or acetamido, inclusive; or a pharmacologically acceptable cation;
wherein $Z_3$ is oxa, h is the integer zero to 3, inclusive; wherein s is the integer zero, one, 2, or 3, and T is chloro, fluoro, trifluoromethyl, alkyl of one to 3 carbon atoms, inclusive, or with the proviso that not more than two T's are other than alkyl.

2. A prostacyclin analog according to claim 1, wherein $Z_3$ is oxa.

3. A prostacyclin analog according to claim 2, wherein $R_8$ is hydroxymethyl.

4. 11-Deoxy-11α-hydroxymethyl-6-hydroxy-16-phenoxy-17,18,19,20-tetranor-PGE₁, a prostacyclin analog according to claim 3.

5. A prostacyclin analog according to claim 2, wherein $R_8$ is hydrogen.

6. 11-Deoxy-6-hydroxy-16-phenoxy-17,18,19,20-tetranor-PGE₁, a prostacyclin analog according to claim 5.

7. A prostacyclin analog according to claim 2, wherein $R_8$ is hydroxy.

8. A prostacyclin analog according to claim 7, wherein ∼OH is beta.

9. 6β-Hydroxy-16-phenoxy-17,18,19,20-tetranor-PGE₁, a prostacyclin analog according to claim 8.

10. A prostacyclin analog according to claim 7, wherein ∼OH is alpha.

11. 6α-Hydroxy-16-phenoxy-17,18,19,20-tetranor-PGE₁, a prostacyclin analog according to claim 10.

12. 6α-Hydroxy-15-methyl-16-phenoxy-17,18,19,20-tetranor-PGE₁, a prostacyclin analog according to claim 10.

13. 6α-Hydroxy-16,16-dimethyl-16-phenoxy-17,18,19,20-tetranor-PGE₁, a prostacyclin analog according to claim 10.

14. A prostacyclin analog according to claim 7, wherein ∼OH is a mixture of α-OH and β-OH.

15. A prostacyclin analog according to claim 14, wherein $Y_1$ is cis-CH=CH—.

16. 6-Hydroxy-cis-13-16-phenoxy-17,18,19,20-tetranor-PGE₁, a prostacyclin analog according to claim 15.

17. A prostacyclin analog according to claim 14, wherein $Y_1$ is —C≡C—.

18. 6-Hydroxy-13,14-didehydro-16-phenoxy-17,18,19,20-tetranor-PGE₁, a prostacyclin analog according to claim 17.

19. A prostacyclin analog according to claim 14, wherein $Y_1$ is trans-CH=C(Hal)—.

20. 6-Hydroxy-14-chloro-16-phenoxy-17,18,19,20-tetranor-PGE$_1$, a prostacyclin analog according to claim 19.

21. A prostacyclin analog according to claim 14, wherein Y$_1$ is —CH$_2$CH$_2$—.

22. 6-Hydroxy-13,14-dihydro-16-phenoxy-17,18,19,20-tetranor-PGE$_1$, a prostacyclin analog according to claim 21.

23. A prostacyclin analog according to claim 14, wherein Y$_1$ is trans-CH=CH—.

24. A prostacyclin analog according to claim 23, wherein Z$_1$ is —(CH$_2$)$_g$—CH$_2$—CF$_2$—.

25. 2,2-Difluoro-6-hydroxy-15-methyl-16-phenoxy-17,18,19,20-tetranor-PGE$_1$, a prostacyclin analog according to claim 24.

26. A prostacyclin analog according to claim 23, wherein Z$_1$ is trans-(CH$_2$)$_g$—CH=CH—.

27. trans-2,3-Didehydro-6-hydroxy-16-phenoxy-17,18,19,20-tetranor-PGE$_1$, a prostacyclin analog according to claim 26.

28. A prostacyclin analog according to claim 23, wherein Z$_1$ is —(CH$_2$)$_g$—CH$_2$—CH$_2$—.

29. A prostacyclin analog according to claim 28, wherein g is one.

30. A prostacyclin analog according to claim 29, wherein s is zero or one and T is chloro, fluoro, or trifluoromethyl.

31. A prostacyclin analog according to claim 30, wherein R$_5$ is methyl.

32. 6-Hydroxy-15-methyl-16-phenoxy-17,18,19,20-tetranor-PGE$_1$, a prostacyclin analog according to claim 31.

33. A prostaglandin analog according to claim 30, wherein R$_5$ is hydrogen.

34. A prostacyclin analog according to claim 33, wherein at least one of R$_3$ and R$_4$ is fluoro.

35. 6-Hydroxy-16,16-difluoro-16-phenoxy-17,18,19,20-tetranor-PGE$_1$, a prostacyclin analog according to claim 34.

36. A prostacyclin analog according to claim 33, wherein at least one of R$_3$ and R$_4$ is methyl.

37. 6-Hydroxy-16,16-dimethyl-16-phenoxy-17,18,19,20-tetranor-PGE$_1$, a prostacyclin analog according to claim 36.

38. A prostacyclin analog according to claim 33, wherein R$_3$ and R$_4$ are both hydrogen.

39. 6-Hydroxy-16-phenoxy-17,18,19,20-tetranor-PGE$_1$, methyl ester, a prostacyclin analog according to claim 38.

40. 6-Hydroxy-16-phenoxy-17,18,19,20-tetranor-PGE$_1$, tris(hydroxymethyl)aminomethane salt, a prostacyclin analog according to claim 38.

41. 6-Hydroxy-16-phenoxy-17,18,19,20-tetranor-PGE$_1$, benzamidophenyl ester, a prostacyclin analog according to claim 38.

42. 6-Hydroxy-16-phenoxy-17,18,19,20-tetranor-PGE$_1$, a prostacyclin analog according to claim 38.

43. A prostacyclin analog according to claim 2, wherein Z$_3$ is —(CH$_2$)$_h$—.

44. A prostacyclin analog according to claim 43, wherein R$_8$ is hydroxymethyl.

45. 11-Deoxy-11α-hydroxymethyl-6-hydroxy-17-phenyl-18,19,20-trinor-PGE$_1$, a prostacyclin analog according to claim 44.

46. A prostacyclin analog according to claim 43, wherein R$_8$ is hydrogen.

47. 11-Deoxy-6-hydroxy-17-phenyl-18,19,20-trinor-PGE$_1$, a prostacyclin analog according to claim 46.

48. A prostacyclin analog according to claim 43, wherein R$_8$ is hydroxy.

49. A prostacyclin analog according to claim 48, wherein ~OH is beta.

50. 6β-Hydroxy-17-phenyl-18,19,20-trinor-PGE$_1$, a prostacyclin analog according to claim 49.

51. A prostacyclin analog according to claim 48, wherein OH is alpha.

52. 6α-Hydroxy-17-phenyl-18,19,20-trinor-PGE$_1$, a prostacyclin analog according to claim 51.

53. 6α-Hydroxy-15-methyl-17-phenyl-18,19,20-trinor-PGE$_1$, a prostacyclin analog according to claim 51.

54. 6α-Hydroxy-16,16-dimethyl-17-phenyl-18,19,20-trinor-PGE$_1$, a prostacyclin analog according to claim 51.

55. A prostacyclin analog according to claim 48, wherein OH is a mixture of α-OH and β-OH.

56. A prostacyclin analog according to claim 55, wherein Y$_1$ is cis-CH=CH—.

57. 6-Hydroxy-cis-13-17-phenyl-18,19,20-trinor-PGE$_1$, a prostacyclin analog according to claim 56.

58. A prostacyclin analog according to claim 55, wherein Y$_1$ is —C≡C—.

59. 6-Hydroxy-13,14-didehydro-17-phenyl-18,19,20-trinor-PGE$_1$, a prostacyclin analog according to claim 58.

60. A prostacyclin analog according to claim 55, wherein Y$_1$ is trans-CH=C(Hal)—.

61. 6-Hydroxy-14-chloro-17-phenyl-18,19,20-trinor-PGE$_1$, a prostacyclin analog according to claim 60.

62. A prostacyclin analog according to claim 55, wherein Y$_1$ is —CH$_2$CH$_2$—.

63. 6-Hydroxy-13,14-dihydro-17-phenyl-18,19,20-trinor-PGE$_1$, a prostacyclin analog according to claim 62.

64. A prostacyclin analog according to claim 55, wherein Y$_1$ is trans-CH=CH—.

65. A prostacyclin analog according to claim 64, wherein Z$_1$ is —(CH$_2$)$_g$—CH$_2$—CF$_2$—.

66. 2,2-Difluoro-6-hydroxy-15-methyl-17-phenyl-18,19,20-trinor-PGE$_1$, a prostacyclin analog according to claim 65.

67. A prostacyclin analog according to claim 64, wherein Z$_1$ is trans-(CH$_2$)$_g$—CH=CH—.

68. trans-2,3-Didehydro-6-hydroxy-17-phenyl-18,19,20-trinor-PGE$_1$, a prostacyclin analog according to claim 67.

69. A prostacyclin analog according to claim 64, wherein Z$_1$ is —(CH$_2$)$_g$—CH$_2$—CH$_2$—.

70. A prostacyclin analog according to claim 69, wherein g is zero.

71. A prostacyclin analog according to claim 70, wherein s is zero or one and T is chloro, fluoro, or trifluoromethyl.

72. A prostacyclin analog according to claim 71, wherein R$_5$ is methyl.

73. 6-Hydroxy-15-methyl-17-phenyl-18,19,20-trinor-PGE$_1$, a prostacyclin analog according to claim 72.

74. A prostacyclin analog according to claim 71, wherein R$_5$ is hydrogen.

75. A prostacyclin analog according to claim 74, wherein at least one of R$_3$ and R$_4$ is fluoro.

76. 6-Hydroxy-16,16-difluoro-17-phenyl-18,19,20-trinor-PGE$_1$, a prostacyclin analog according to claim 75.

77. A prostacyclin analog according to claim 74, wherein at least one of R$_3$ and R$_4$ is methyl.

78. 6-Hydroxy-16,16-dimethyl-17-phenyl-18,19,20-trinor-PGE$_1$, a prostacyclin analog according to claim 77.

79. A prostacyclin analog according to claim 74, wherein $R_3$ and $R_4$ are both hydrogen.

80. 6-Hydroxy-17-phenyl-18,19,20-trinor-$PGE_1$, methyl ester, a prostacyclin analog according to claim 79.

81. 6-Hydroxy-17-phenyl-18,19,20-trinor-$PGE_1$, tris(-hydroxymethyl)aminomethane salt, a prostacyclin analog according to claim 79.

82. 6-Hydroxy-17-phenyl-18,19,20-trinor-$PGE_1$, benzamidophenyl ester, a prostacyclin analog according to claim 79.

83. 6-Hydroxy-17-phenyl-18,19,20-trinor-$PGE_1$, a prostacyclin analog according to claim 79.

UNITED STATES PATENT AND TRADEMARK OFFICE
CERTIFICATE OF CORRECTION

PATENT NO. : 4,147,877
DATED : April 3, 1979
INVENTOR(S) : Herman W. Smith

It is certified that error appears in the above-identified patent and that said Letters Patent are hereby corrected as shown below:

Column 1, line 27, claim 1, after line 7, insert -- wherein $R_8$ is hydroxy, hydroxymethyl, or hydrogen; --.

Column 2, line 22, "$Z_3$ is oxa" should read -- $Z_3$ is oxa or $-(CH_2)_h-$, --; line 59, "cis-CH≡CH-." read -- cis-CH=CH-. --.

Column 4, line 8, "wherein OH" should read -- wherein ⌇OH --.

Column 4, line 17, "wherein OH" should read -- wherein ⌒OH --.

Signed and Sealed this

*Fourth* Day of *September 1979*

[SEAL]

*Attest:*

*Attesting Officer*

LUTRELLE F. PARKER
*Acting Commissioner of Patents and Trademarks*